United States Patent [19]

Grélat

[11] 3,978,094

[45] Aug. 31, 1976

[54] PROCESS FOR THE MANUFACTURE OF 1,4-DIAMINO-5-NITROANTHRAQUINONE

[75] Inventor: Maurice Grélat, Bettingen, Switzerland

[73] Assignee: Ciba-Geigy AG, Basel, Switzerland

[22] Filed: Nov. 5, 1975

[21] Appl. No.: 629,157

Related U.S. Application Data

[63] Continuation of Ser. No. 491,438, July 24, 1974, abandoned.

[30] Foreign Application Priority Data

July 31, 1973 Switzerland................ 11144/73

[52] U.S. Cl................................. 260/378; 260/369
[51] Int. Cl.²................... C07C 97/12; C07C 97/24
[58] Field of Search...................... 260/378

[56] References Cited

UNITED STATES PATENTS

| 3,235,549 | 2/1966 | Broussalian | 260/243 R |
| 3,818,052 | 6/1974 | Hohmann | 260/378 |

FOREIGN PATENTS OR APPLICATIONS

| 1,107,869 | 1/1966 | United Kingdom | 260/378 |
| 1,033,773 | 6/1966 | United Kingdom | 260/378 |

OTHER PUBLICATIONS

Bios. Final Report No. 1484, p. 20.

*Primary Examiner*—Paul F. Shaver
*Attorney, Agent, or Firm*—Joseph G. Kolodny; Edward McC. Roberts; Prabodh I. Almaula

[57] ABSTRACT

A process for the manufacture of 1,4-diamino-5-nitroanthraquinone from 1,4-diaminoanthraquinone by nitration with mixed nitric and sulphuric acid, before which nitration a masking of the two amino groups to form 1,9-4,10-anthraauinone-disulphonimide takes place, this intermediate being in turn split by hydrolysis after the nitration, which process comprises carrying out the masking of the 1,4-diaminoanthraquinone to form 1,9-4,10 anthraquinone-disulphonimide in concentrated sulphuric acid which can optionally contain dissolved $SO_3$, or in concentrated phosphoric acid using liquid sulphur trioxide.

3 Claims, No Drawings

PROCESS FOR THE MANUFACTURE OF 1,4-DIAMINO-5-NITROANTHRAQUINONE

This is a continuation of application Ser. No. 491,438, filed on July 24, 1974 now abandoned.

The present invention provides a process for the manufacture of 1,4-diamino-5-nitroanthraquinone by nitrating 1,4-diamino-anthraquinone with nitrosulphuric acid via the intermediate 1,9-4,10-anthraquinone-disulphonimide using sulphur trioxide as masking reagent for the formation of the anthraquinone-disulphonimide.

The reaction proceeds according to the reaction scheme:

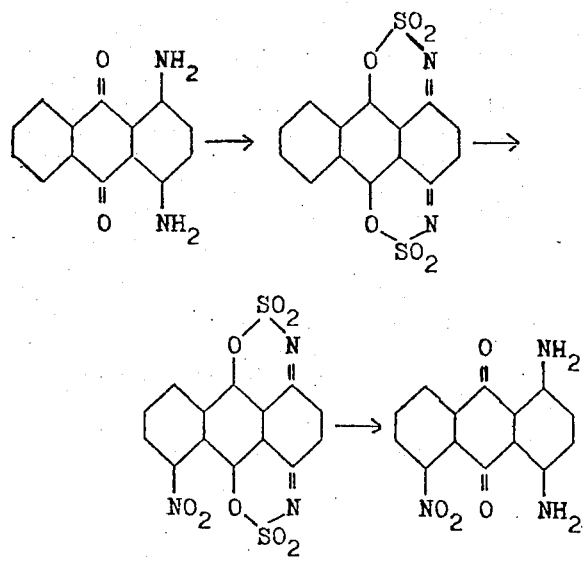

The 1,4-diamino-5-nitroanthraquinone constitutes a valuable violet dyestuff.

The process according to the steps of the above reaction scheme is known and has been described e.g. in BIOS Final Report No. 1484, p. 20.

Hitherto, oleum has been used to mask the amino groups of the 1,4-diamino-anthraquinone.

After the subsequent nitration with nitrosulphuric acid has been effected, the disulphonimide protective groups formed as intermediate are split by hydrolysis using sulphuric acid.

However, the nitration of 1,4-diamino-anthraquinone to form 1,4-diamino-5-nitro-anthraquinone by this known process requires large amounts of sulphuric acid or oleum which are used partly as reaction medium and partly as masking reagent.

According to the particulars of the BIOS Final Report, the following amounts of sulphuric acid or oleum are required for a batch of 100 kg of 1,4-diaminoanthraquinone:

a. 700.0 kg of 65% oleum as solvent medium for 1,4-diaminoanthraquinone and as masking reagent of the formation of 1,9-4,10-anthraquinone-disulphonimide.

b. 293.0 kg of 78% $H_2SO_4$ for diluting the reaction medium according to the masking reaction.

c. 86.5 kg of 100% $H_2SO_4$ in the form of nitration mixed acid containing 28% $HNO_3$.

d. 330.0 kg of 38% $H_2SO_4$ for washing the 5-nitro-1,9-4,10-anthraquinone-disulphonimide.

If the $SO_3$ content of the oleum is converted into sulphuric acid, then 1,160.0 kg of sulphuric acid are required for the above 100 kg batch in the first two steps of the process.

This process sulphuric acid poses a major ecological problem since, after termination of the reaction cycle, it can only be reused in the rarest instances. Moreover, for commercial reasons it is preferable to use small amounts of ballast materials which are essential for use in a reaction.

The present invention is based on the surprising observation that, on using preferably liquid sulphur trioxide as masking reagent, substantially smaller amounts of waste sulphuric acid occur than in known processes. So great is the effect that it is possible to save about 50% of the sulphuric acid normally required. This is all the more unexpected since the oleum normally used already constitutes a solution of sulphur trioxide in sulphuric acid.

The new process for the manufacture of 1,4-diamino-5-nitroanthraquinone from 1,4-diaminoanthraquinone by nitration with a mixture of nitric and sulphuric acid, before which nitration a masking of both amino groups to form, 1,9-4-10-anthraquinone-disulphonimide occurs, this intermediate being in turn split by hydrolysis after the nitration, consists in carrying out the masking of the 1,4-diaminoanthraquinone to form the 1,9-4,10-anthraquinone-disulphonimide in concentrated sulphuric acid which can optionally contain dissolved $SO_3$, or in concentrated phosphoric acid using liquid sulphur trioxide. It is sufficient to use 100% sulphuric acid for the step of dissolving or suspending the 1,4-diaminoanthraquinone. In this case, it is then necessary to use more sulphur trioxide for the masking reaction. It is therefore desirable to use from the outset oleum in concentrations ranging from 20% to 45%, in particular from 25% to 35%.

The sole criterion for amount and concentration of the oleum employed is the most satisfactory means technically of bringing about the step of dissolving or suspending the 1,4-diaminoanthraquinone, the quantitative ratio of sulphuric or phosphoric acid to diaminoanthraquinone advantageously being 2:1 to 4:1.

The process according to the invention is carried out, for example, in the following manner:

In the above mentioned step of dissolving or suspending, commercial 1,4-diaminoanthraquinone is added with stirring to 40% oleum with such rapidity that the temperature does not exceed 80°C. Temperature between 40° and 60°C are advantageous. Liquid sulphur trioxide is added to this solution or suspension, and in doing so the stated temperatures are likewise kept.

The amount of $SO_3$ added can so vary that a final $SO_3$ concentration of 35%–60%, desirably 40%–45%, is attained. The reaction mass is then stirred for a time at the stated temperatures and subsequently cooled to room temperature.

The subsequent nitration with mixed nitric and sulphuric acid proceeds best if the concentration of $SO_3$ in the reaction mass is between 5% and 20%. For this reason it is necessary to dilute the reaction mass with water before the addition of the mixed acid.

The nitration is carried out with a mixture of nitric and sulphuric acid as used in the art for nitration reactions. An acid mixture containing 50% of $NHO_3$ and 50% of $H_2SO_4$ is customary and desirable.

It is also possible to use other acid mixtures, for example with $HNO_3$ content between 20% and 80%. The amount of acid mixture added should not exceed 50% surplus over theory; a surplus of 30%–40% is used with advantage.

At low $HNO_3$ concentrations the nitration reaction proceeds too slowly, and at too high concentrations too energetically. The addition of the acid mixture is effected continuously at such a speed the reaction temperature does not exceed 25°C and it may be necessary to cool. Upon completion of the addition, stirring is continued for several hours.

In order to be able to isolate the 5-nitro-1,9,-4,10-anthraquinone-disulphonimide step, water is added to the reaction mixture until the solubility of the product in the reaction medium is so greatly reduced that it crystallises out. Ordinarily, dilution is effected to an 80%–90% $H_2SO_4$ content. In this operation too a temperature limit of 30°C is to be observed.

The crystallised product is isolated from the reaction medium by suction filtration or by other methods of separation, washed first with small amounts of 60% sulphuric acid and then with water until neutral, dried, or hydrolysed direct to 1,4-diamino-5-nitroanthraquinone by known methods, e.g. with 96% $H_2SO_4$ at 120°C. The yields are between 70% and 80%.

The following tabular comparison shows the difference between known processes and the process according to the invention in respect of process or solution sulphuric acid used. The $SO_3$ values are converted to $H_2SO_4$ in each case and each batch is one of 100 kg of 1,4-diaminoanthraquinone.

The reaction mixture is further stirred for 1 hour at 15°–20°C. The crystallised product is collected by suction filtration, washed first with some 60% sulphuric acid and then with water until neutral. The product is then dried to yield about 60 g of 5-nitro-1,9-4,10-anthraquinone-disulphonamide (=72% of theory) which can be hydrolysed to 1,4-diamino-5-nitroanthraquinone in known manner, e.g. with 96% sulphuric acid at 120°C.

EXAMPLE 2

23.8 g of 1,4-diaminoanthraquinone are added with stirring to 50 g of 100% phosphoric acid and 120 g of sulphur trioxide are added dropwise at 55°–60°C over the course of 90 minutes. Stirring of the reaction mixture is continued for 4 hours at 60°C and the mixture is then cooled to room temperature. With cooling, 13.5 ml of water are added dropwise at a maximum temperature of 25°C. At this same temperature, 17.5 g of 50% mixed nitric and sulphuric acid are added dropwise over the course of 90 minutes and stirring is continued for 4 hours. With cooling, 40 ml of water are added dropwise, in the process of which the temperature should not exceed 30°C. Stirring of the reaction mixture is continued for 1 hour at 15°–25°C. The crystallised product is collected by suction filtration, washed first with 60% sulphuric acid and then with water until the filtrate is neutral. The product is dried to yield about 30 g of 5-nitro-1,9-4,10-anthraquinone-disulphonimide which can be hydrolysed to 1,4-diamino-5-

| 1,4-diamino-anthraquinone | BIOS — Process 100 kg | | | Process according to the invention with $SO_3$ 100 kg | | | |
|---|---|---|---|---|---|---|---|
| | | $SO_3$ | $H_2SO_4$ | | | $SO_3$ | $H_2SO_4$ |
| a) Oleum 65% | 500 kg | 325,0 kg | 175,0 kg | a) Oleum 35% | 283,5 kg | 99,3 kg | 184,1 kg |
| | 200 kg | 130,0 kg | 70,0 kg | $SO_3$ | 218,0 kg | 218,0 kg | |
| b) $H_2SO_4$ 78% | 293 kg | | 228,5 kg | — | | | |
| c) Mixed acid 28% $HNO_3$ | 120 kg | | 86,5 kg | c) Mixed acid 50% | 73,6 kg | | 36,8 kg |
| d) Washing acid 38% | 330 kg | | 125,5 kg | d) Washing acid 60% | 211,8 kg | | 127,1 kg |
| — bound $SO_3$ (as disulphone) | | −67,0 kg | | — bound $SO_3$ (as disulphone) | | −67,0 kg | |
| | | 388,0 kg = | 475,0 kg | | | 250,3 kg = | 303,0 kg |
| Total amount of sulphuric acid | | | 1160,0 kg | Total amount of sulphuric acid | | | 651,0 kg |

The following examples illustrate the invention, the parts and percentages being by weight unless otherwise stated, and the relationship between parts by weight and parts volume being the same as that between the gram and the cubic centimeter.

EXAMPLE 1

47.6 g of 1,4-diaminoanthraquinone are added with stirring to 135 g of 35% oleum. In doing so, the temperature may not exceed 60°C. The mixture is stirred for 30 minutes at 55°C to 60°C and at this temperature 103 g of liquid sulphur trioxide are added over the course of 90 minutes. The reaction mixture is further stirred at 60°C for 4 hours and then allowed to cool to room temperature. With cooling, 11.8 ml of water are added dropwise at a maximum temperature of 25°C. The batch is stirred at 20°C–25°C for 45 minutes. At this temperature, 35.2 g of 50% mixed nitric and sulphuric acid are dropwise over the course of 2½ hours and stirring is continued for 4 hours. Then 51 ml of water are added dropwise with cooling, in the process of which the temperature may not exceed 25°C–30°C.

nitro-anthraquinone in known manner, e.g. with 96% sulphuric acid at 120°C.

I claim:
1. In a process for the manufacture of 1,4-diamino-5-nitro-anthraquinone from 1,4-diaminoanthraquinone by nitration with a mixture of 50% nitric acid and 50% sulphuric acid, before which nitration a masking of the two amino groups to form 1,9-4,10-anthraquinone-disulphonamide takes place, this intermediate being in turn split by hydrolysis after the nitration, the improvement comprising the steps of (1) dissolving or suspending 1,4-diaminoanthraquinone in concentrated sulphuric acid or in concentrated sulphuric acid containing dissolved sulphur trioxide or in concentrated phosphoric acid, (2) carrying out the masking by adding liquid sulphur trioxide to the solution or suspension in such an amount that a final sulphur trioxide concentration of 35–60% is attained in said solution or suspension, and (3) nitrating by adding to said solution or suspension a mixture of 50% nitric acid and 50% sulphuric acid, said mixture of acids being in amounts below 100 kilogram per 100 kilogram of 1,4-diaminoanthraquinone.

2. A process of claim 1, wherein the 1,4-diaminoanthraquinone is dissolved or suspended in concentrated sulphuric acid containing 20–40% of the dissolved sulphur trioxide.

3. A process of claim 2, wherein the 1,4-diaminoanthraquinone is dissolved or suspended in concentrated sulphuric acid containing 30–35% of dissolved sulphur trioxide.

\* \* \* \* \*